(12) United States Patent
Tunheim et al.

(10) Patent No.: US 9,182,355 B2
(45) Date of Patent: *Nov. 10, 2015

(54) SYSTEMS AND METHODS FOR MONITORING A FLOW PATH

(75) Inventors: Ola Tunheim, Bryne (NO); Robert P. Freese, Pittsboro, NC (US); James R. MacLennan, Aberdeen (GB); Laurence James Abney, Rogaland (NO); Thomas Idland, Rogaland (NO)

(73) Assignee: Halliburton Energy Services, Inc., Houston, TX (US)

( * ) Notice: Subject to any disclaimer, the term of this patent is extended or adjusted under 35 U.S.C. 154(b) by 260 days.

This patent is subject to a terminal disclaimer.

(21) Appl. No.: 13/616,106

(22) Filed: Sep. 14, 2012

(65) Prior Publication Data

US 2013/0033701 A1     Feb. 7, 2013

Related U.S. Application Data

(63) Continuation-in-part of application No. 13/198,915, filed on Aug. 5, 2011, which is a continuation-in-part of application No. 13/198,950, filed on Aug. 5, 2011, which is a continuation-in-part of application No.

(Continued)

(51) Int. Cl.
*G01N 21/85*     (2006.01)
(52) U.S. Cl.
CPC ...................... *G01N 21/85* (2013.01)
(58) Field of Classification Search
CPC ................ G01N 21/636; G01N 21/8507
See application file for complete search history.

(56) References Cited

U.S. PATENT DOCUMENTS

| | | |
|---|---|---|
| 5,431,227 A | 7/1995 | Montgomery et al. |
| 5,680,900 A | 10/1997 | Nguyen et al. |
| 5,737,076 A | 4/1998 | Glaus et al. |

(Continued)

FOREIGN PATENT DOCUMENTS

| | | |
|---|---|---|
| EP | 1969326 | 9/2008 |
| EP | 2087328 | 8/2009 |

(Continued)

OTHER PUBLICATIONS

International Preliminary Report on Patentability for PCT/US2012/046892 dated Feb. 20, 2014.

(Continued)

*Primary Examiner* — Angela M DiTrani
*Assistant Examiner* — Ashish Varma
(74) *Attorney, Agent, or Firm* — McDermott Will & Emery LLP; Scott Brown (57) ABSTRACT

Disclosed are systems and methods for analyzing a flow of a fluid at two or more discrete locations to determine the concentration of a substance therein. One method of determining a characteristic of a fluid may include containing a fluid within a flow path that provides at least a first monitoring location and a second monitoring location, generating a first output signal corresponding to the characteristic of the fluid at the first monitoring location with a first optical computing device, generating a second output signal corresponding to the characteristic of the fluid at the second monitoring location with a second optical computing device, receiving first and second output signals from the first and second optical computing devices, respectively, with a signal processor, and determining a difference between the first and second output signals with the signal processor.

22 Claims, 2 Drawing Sheets

Related U.S. Application Data

13/198,972, filed on Aug. 5, 2011, which is a continuation-in-part of application No. 13/204,005, filed on Aug. 5, 2011, which is a continuation-in-part of application No. 13/204,046, filed on Aug. 5, 2011, which is a continuation-in-part of application No. 13/204,123, filed on Aug. 5, 2011, now Pat. No. 8,960,294, which is a continuation-in-part of application No. 13/204,165, filed on Aug. 5, 2011, which is a continuation-in-part of application No. 13/204,213, filed on Aug. 5, 2011, which is a continuation-in-part of application No. 13/204,294, filed on Aug. 5, 2011.

(56) References Cited

U.S. PATENT DOCUMENTS

| | | |
|---|---|---|
| 5,996,690 A | 12/1999 | Shaw et al. |
| 6,016,191 A | 1/2000 | Ramos et al. |
| 6,091,504 A | 7/2000 | Walker et al. |
| 6,198,531 B1 | 3/2001 | Myrick et al. |
| 6,268,911 B1 * | 7/2001 | Tubel et al. .................. 356/72 |
| 6,529,276 B1 | 3/2003 | Myrick |
| 6,729,400 B2 | 5/2004 | Mullins et al. |
| 6,755,978 B2 | 6/2004 | Oddie |
| 6,880,566 B2 | 4/2005 | Newman |
| 7,123,844 B2 | 10/2006 | Myrick |
| 7,138,156 B1 | 11/2006 | Myrick et al. |
| 7,236,237 B2 | 6/2007 | Schmilovitch et al. |
| 7,332,094 B2 | 2/2008 | Abney et al. |
| 7,472,748 B2 | 1/2009 | Gdanski et al. |
| 7,623,233 B2 | 11/2009 | Freese et al. |
| 7,671,973 B2 | 3/2010 | Van Beek et al. |
| 7,697,141 B2 | 4/2010 | Jones et al. |
| 7,712,527 B2 | 5/2010 | Roddy |
| 7,789,171 B2 | 9/2010 | Grayson et al. |
| 7,834,999 B2 | 11/2010 | Myrick et al. |
| 7,911,605 B2 | 3/2011 | Myrick et al. |
| 7,920,258 B2 | 4/2011 | Myrick et al. |
| 7,934,556 B2 | 5/2011 | Clark et al. |
| 8,049,881 B2 | 11/2011 | Myrick et al. |
| 8,141,633 B2 | 3/2012 | Hampton et al. |
| 8,253,619 B2 | 8/2012 | Holbrook et al. |
| 8,345,234 B2 | 1/2013 | Myrick et al. |
| 8,547,556 B2 | 10/2013 | Irani |
| 8,780,352 B2 | 7/2014 | Freese et al. |
| 8,823,939 B2 | 9/2014 | Freese et al. |
| 8,879,053 B2 | 11/2014 | Freese et al. |
| 8,908,165 B2 | 12/2014 | Tunheim et al. |
| 8,941,046 B2 | 1/2015 | Freese et al. |
| 8,960,294 B2 | 2/2015 | Freese et al. |
| 8,997,860 B2 | 4/2015 | Freese et al. |
| 9,013,698 B2 | 4/2015 | Freese et al. |
| 9,013,702 B2 | 4/2015 | Freese et al. |
| 9,019,501 B2 | 4/2015 | Freese et al. |
| 9,074,990 B2 | 7/2015 | Freese et al. |
| 2001/0020675 A1 | 9/2001 | Tubel et al. |
| 2002/0023752 A1 | 2/2002 | Qu et al. |
| 2002/0071121 A1 | 6/2002 | Ortyn et al. |
| 2002/0109080 A1 | 8/2002 | Tubel et al. |
| 2003/0056581 A1 | 3/2003 | Turner et al. |
| 2003/0143580 A1 | 7/2003 | Straus |
| 2003/0145988 A1 | 8/2003 | Mullins et al. |
| 2004/0045705 A1 | 3/2004 | Gardner et al. |
| 2004/0129884 A1 | 7/2004 | Boyle et al. |
| 2004/0179194 A1 | 9/2004 | Schmilovitch et al. |
| 2006/0102343 A1 | 5/2006 | Skinner et al. |
| 2006/0142955 A1 | 6/2006 | Jones et al. |
| 2006/0158734 A1 | 7/2006 | Schuurmans et al. |
| 2007/0095528 A1 | 5/2007 | Ziauddin et al. |
| 2007/0114372 A1 | 5/2007 | Lievois et al. |
| 2007/0177240 A1 | 8/2007 | Van Beek et al. |
| 2007/0215385 A1 | 9/2007 | Anderson |
| 2007/0281870 A1 | 12/2007 | Robb et al. |
| 2007/0282647 A1 | 12/2007 | Freese et al. |
| 2007/0291251 A1 | 12/2007 | Rensen et al. |
| 2008/0000635 A1 | 1/2008 | Rioufol et al. |
| 2008/0041594 A1 | 2/2008 | Boles et al. |
| 2008/0094623 A1 | 4/2008 | Schuurmans et al. |
| 2008/0133193 A1 | 6/2008 | Gdanski et al. |
| 2008/0217011 A1 | 9/2008 | Pauls et al. |
| 2008/0231849 A1 | 9/2008 | Myrick et al. |
| 2008/0262737 A1 | 10/2008 | Thigpen et al. |
| 2008/0276261 A1 | 11/2008 | Myrick et al. |
| 2008/0309930 A1 | 12/2008 | Rensen |
| 2009/0002697 A1 | 1/2009 | Freese et al. |
| 2009/0015819 A1 | 1/2009 | Van Beek et al. |
| 2009/0033933 A1 | 2/2009 | Myrick et al. |
| 2009/0073433 A1 | 3/2009 | Myrick et al. |
| 2009/0087912 A1 | 4/2009 | Ramos et al. |
| 2009/0097024 A1 | 4/2009 | Blackburn et al. |
| 2009/0140144 A1 | 6/2009 | Myrick et al. |
| 2009/0154288 A1 | 6/2009 | Heathman |
| 2009/0182693 A1 | 7/2009 | Fulton et al. |
| 2009/0205821 A1 | 8/2009 | Smith |
| 2009/0216504 A1 | 8/2009 | Priore et al. |
| 2009/0219512 A1 | 9/2009 | Myrick et al. |
| 2009/0219538 A1 | 9/2009 | Myrick et al. |
| 2009/0219539 A1 | 9/2009 | Myrick et al. |
| 2009/0219597 A1 | 9/2009 | Myrick et al. |
| 2009/0245718 A1 | 10/2009 | Li et al. |
| 2009/0250613 A1 | 10/2009 | Myrick et al. |
| 2009/0299946 A1 | 12/2009 | Myrick et al. |
| 2009/0305330 A1 | 12/2009 | Kroon et al. |
| 2009/0316150 A1 | 12/2009 | Myrick et al. |
| 2010/0006292 A1 | 1/2010 | Boles et al. |
| 2010/0042348 A1 | 2/2010 | Bakker |
| 2010/0050905 A1 | 3/2010 | Lewis et al. |
| 2010/0051266 A1 | 3/2010 | Roddy et al. |
| 2010/0051275 A1 | 3/2010 | Lewis et al. |
| 2010/0073666 A1 | 3/2010 | Perkins et al. |
| 2010/0084132 A1 | 4/2010 | Noya et al. |
| 2010/0141952 A1 | 6/2010 | Myrick et al. |
| 2010/0148785 A1 * | 6/2010 | Schaefer et al. .............. 324/338 |
| 2010/0149523 A1 | 6/2010 | Heideman et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0245096 A1 | 9/2010 | Jones et al. |
| 2010/0265509 A1 | 10/2010 | Jones et al. |
| 2010/0269579 A1 | 10/2010 | Lawrence et al. |
| 2010/0285105 A1 | 11/2010 | Radianingtyas |
| 2010/0302539 A1 | 12/2010 | Myrick et al. |
| 2010/0305741 A1 | 12/2010 | Myrick |
| 2010/0326659 A1 | 12/2010 | Schultz et al. |
| 2010/0328669 A1 | 12/2010 | Myrick et al. |
| 2011/0042320 A1 | 2/2011 | Allen |
| 2011/0048708 A1 | 3/2011 | Glasbergen et al. |
| 2011/0163046 A1 | 7/2011 | Neal et al. |
| 2011/0166046 A1 | 7/2011 | Weaver et al. |
| 2011/0197662 A1 * | 8/2011 | McAlister .................. 73/61.59 |
| 2011/0199610 A1 | 8/2011 | Myrick et al. |
| 2011/0312012 A1 | 12/2011 | Skinderso et al. |
| 2012/0000643 A1 | 1/2012 | Bruun et al. |
| 2012/0135396 A1 | 5/2012 | McDevitt et al. |
| 2012/0150451 A1 | 6/2012 | Skinner et al. |
| 2012/0160329 A1 | 6/2012 | MacKenzie et al. |
| 2012/0250017 A1 | 10/2012 | Morys et al. |
| 2013/0031964 A1 | 2/2013 | Tunheim et al. |
| 2013/0031970 A1 | 2/2013 | Freese et al. |
| 2013/0031971 A1 | 2/2013 | Freese et al. |
| 2013/0031972 A1 | 2/2013 | Freese et al. |
| 2013/0032333 A1 | 2/2013 | Freese et al. |
| 2013/0032340 A1 | 2/2013 | Freese et al. |
| 2013/0032344 A1 | 2/2013 | Freese et al. |
| 2013/0032345 A1 | 2/2013 | Freese et al. |
| 2013/0033701 A1 | 2/2013 | Tunheim et al. |
| 2013/0033702 A1 | 2/2013 | Tunheim et al. |

(56) References Cited

U.S. PATENT DOCUMENTS

| | | | |
|---|---|---|---|
| 2013/0034842 A1 | 2/2013 | Tunheim et al. | |
| 2013/0284895 A1 | 10/2013 | Freese et al. | |
| 2014/0263974 A1 | 9/2014 | Freese et al. | |

FOREIGN PATENT DOCUMENTS

| | | |
|---|---|---|
| EP | 2140238 | 1/2010 |
| EP | 2320027 A1 | 5/2011 |
| FR | 2954563 A1 | 6/2011 |
| GB | 2353310 A | 2/2001 |
| JP | 2009284813 A | 12/2009 |
| WO | 9850680 A2 | 11/1998 |
| WO | 2004018840 A1 | 3/2004 |
| WO | 2006137902 A2 | 12/2006 |
| WO | 2007064575 | 6/2007 |
| WO | 2006137902 A3 | 12/2007 |
| WO | 2008121715 A1 | 10/2008 |
| WO | 2009055200 A2 | 4/2009 |
| WO | 2009055220 A2 | 4/2009 |
| WO | 2009077758 A1 | 6/2009 |
| WO | 2011063086 A1 | 5/2011 |
| WO | 2014042909 A1 | 3/2014 |
| WO | 2014042933 A1 | 3/2014 |
| WO | 2014043010 A1 | 3/2014 |
| WO | 2014043050 A1 | 3/2014 |
| WO | 2014043057 A1 | 3/2014 |

OTHER PUBLICATIONS

International Search Report and Written Opinion for PCT/US2012/044148 dated Oct. 4, 2012.
Official Action for Australian Patent Application 2012294881 dated May 22, 2014.
International Search Report and Written Opinion for PCT/US2012/047065 dated Jul. 16, 2013.
International Search Report and Written Opinion for PCT/US2012/045677 dated Jul. 16, 2013.
Myrick, et al. "Spectral Tolerance Determination for Multivariate Optical Element Design," Fresenuis' Journal of Analytical Chemistry, 369:2001; pp. 351-355.
Gdanski et al., "A New Model for Matching Fracturing Fluid Flowback Composition," 2007 SPE Hydraulic Fracturing Technology Conference held in College Station, Texas, SPE 106040.
Gdanski et al., "Using Lines-of-Solutions to Understand Fracture Conductivity and Fracture Cleanup," SPE Production and Operations Symposium held in Oklahoma City, OK, 2011, SPE 142096.
Ramachandran et al., "Chemical Kinetics in Real Time: Using the Differential Rate Law and Discovering the Reaction Orders," A Physical chemistry Laboratory Experiment, Journal of chemical Education; 1996, pp. 686-689.
International Search Report and Written Opinion for PCT/US2013/057832 dated Nov. 22, 2013.
International Search Report and Written Opinion for PCT/US2013/058041 dated Dec. 2, 2013.
International Search Report and Written Opinion for PCT/US2013/058700 dated Dec. 6, 2013.
International Search Report and Written Opinion for PCT/US2013/058864 dated Dec. 16, 2013.
Official Action for Australian Patent Application No. 2013252855 dated Apr. 15, 2015.
Dai et al., Molecular Factor Computing for Predictive Spectroscopy, Pharmaceutical Research, vol. 24, No. 8, 2007, pp. 1441-1449.
Mendendorp J., et al., Application of Integrated Sensing and Processing in Spectroscopic Imaging and Sensing, Journal of Chemometrics, vol. 19, 2005, pp. 533-542.
Official Action for Australian Patent Application No. 2013 252841 dated Nov. 10, 2014.
Official Action for Australian Patent Application No. 2013 252881 dated Nov. 12, 2014.
Official Action for Singapore Patent Application No. 11201500780V dated Jun. 16, 2015.

* cited by examiner

SYSTEMS AND METHODS FOR MONITORING A FLOW PATH

CROSS-REFERENCE TO RELATED APPLICATIONS

The present application claims priority to and is a continuation-in-part application of co-owned U.S. patent application Ser. Nos. 13/198,915; 13/198,950; 13/198,972; 13/204,005; 13/204,046; 13/204,123 now U.S. Pat. No. 8,960,294; Ser. Nos. 13/204,165; 13/204,213; and 13/204,294, each of which were filed on Aug. 5, 2011. The contents of each priority application are hereby incorporated by reference.

BACKGROUND

The present invention relates to optical analysis systems and methods for analyzing fluids and, in particular, systems and methods for analyzing a flow of a fluid at two or more discrete locations to determine a characteristic of a substance in the fluid.

In the oil and gas industry, several flow assurance techniques are employed to monitor the formation of both organic and inorganic deposits in flowlines and pipelines. These deposits can seriously impede the productivity of wells by reducing the near wellbore permeability of producing formations and progressively restrict the diameter of the connected flow conduits, flowlines and pipelines. Problems relating to flow assurances cost the oil industry billions of dollars worldwide for prevention and remediation.

Flow assurance problems are most often related to paraffin waxes and asphaltenes, which are typically caused by changes in the pressure and temperature of the produced fluids at or near the wellbore or in surface flow conduits. As the waxes and asphaltenes precipitate out of the fluid, the precipitates can accumulate and tend to restrict or clog flowlines and pipelines. Removing the precipitates can be done using solvent washes, although, in some cases, the disposal of certain solvents after cleaning presents increasing environmental concerns. In other applications, the precipitates are removed by pipeline grinding, scraping or pigging operations undertaken by an inline tool/device/robot. In extreme cases, this may require that the flowline or pipeline be shut down for a period of time and, in the case of a total blockage, can even require removal of the entire pipeline altogether.

Calcium carbonate scale is usually formed by changes in the pressure and temperature of produced water at or near the wellbore and within the production tubing/flow conduits. Barium, strontium and calcium sulfate scales are usually formed by the mixing of different formation water and also the mixing of formation water and seawater that is injected into producing wells. Scale formation may be partly prevented by water shut-off treatments and the use of scale inhibitors. Once formed, scale can be removed only with some difficulty, such as by dissolving the scale, where applicable, using mineral acids and specially-designed dissolvers. In extreme cases, the scale must be removed by either inline milling operations or removing and replacing the affected flowline or pipeline altogether.

Hydrates lattice compounds of methane and water are crystals which, if formed, may also foul or block flowlines and pipelines. Aromatics and naphthanates when combined with water can cause the formation of foam and/or emulsions that may also cause flow restriction or pipeline interruption. Reservoir erosion can also adversely affect production by adding particulates to the stream and altering subsurface flow characteristics.

Those skilled in the art will readily recognize the importance in accurately determining the effectiveness of treatments designed to counteract asphaltenes, wax, scale, corrosion, as well as monitoring sand/chalk loss, all of which can adversely affect hydrocarbon production. In some cases, production of a well from a particular reservoir can be permanently damaged by flow problems making prevention essential to proper reservoir management. Accordingly, identifying flow assurance issues before they occur will mitigate costly corrective action.

SUMMARY OF THE INVENTION

The present invention relates to optical analysis systems and methods for analyzing fluids and, in particular, systems and methods for analyzing a flow of a fluid at two or more discrete locations to determine a characteristic of a substance in the fluid.

In some aspects of the disclosure, a system is disclosed. The system may include a flow path containing a fluid and providing at least a first monitoring location and a second monitoring location, a first optical computing device arranged at the first monitoring location and having a first integrated computational element configured to optically interact with the fluid and convey optically interacted light to a first detector which generates a first output signal corresponding to a characteristic of the fluid at the first monitoring location, a second optical computing device arranged at the second monitoring location and having a second integrated computational element configured to optically interact with the fluid and convey optically interacted light to a second detector which generates a second output signal corresponding to the characteristic of the fluid at the second location, and a signal processor communicably coupled to the first and second detectors and configured to receive the first and second output signals and determine a difference between the first and second output signals.

In other aspects of the disclosure, a method of determining a characteristic of a fluid is disclosed. The method may include containing a fluid within a flow path that provides at least a first monitoring location and a second monitoring location, generating a first output signal corresponding to the characteristic of the fluid at the first monitoring location with a first optical computing device, the first optical computing device having a first integrated computational element configured to optically interact with the fluid and thereby convey optically interacted light to a first detector which generates the first output signal, generating a second output signal corresponding to the characteristic of the fluid at the second monitoring location with a second optical computing device, the second optical computing device having a second integrated computational element configured to optically interact with the fluid and thereby convey optically interacted light to a second detector which generates the second output signal, receiving the first and second output signals with a signal processor communicably coupled to the first and second detectors, and determining a difference between the first and second output signals with the signal processor.

In yet other aspects of the disclosure, another system is disclosed. The system may include a first flow path containing a first fluid and providing a first monitoring location, a second flow path containing a second fluid and providing a second monitoring location, the first and second flow paths being combined downstream into a common flow path conveying the first and second fluids as a combined fluid, a first optical computing device arranged at the first monitoring location and having a first integrated computational element configured to optically interact with the first fluid and generate a first output signal corresponding to a characteristic of the first fluid, a second optical computing device arranged at the second monitoring location and having a second integrated computational element configured to optically interact with the fluid and generate a second output signal corresponding to the characteristic of the second fluid, and a signal processor communicably coupled to the first and optical computing devices and configured to receive and determine a difference between the first and second output signals.

In yet further aspects of the disclosure, another method of determining a characteristic of a fluid is disclosed. The method may include containing a first fluid within a first flow path that provides a first monitoring location, containing a second fluid within a second flow path that provides a second monitoring location, the first and second flow paths being combined downstream into a common flow path conveying the first and second fluids as a combined fluid, optically interacting a first integrated computational element with the first fluid to generate a first output signal corresponding to a characteristic of the first fluid, optically interacting a second integrated computational element with the second fluid to generate a second output signal corresponding to a characteristic of the second fluid, receiving the first and second output signals with a signal processor, and determining a difference between the first and second output signals with the signal processor.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present invention relates to optical analysis systems and methods for analyzing fluids and, in particular, systems and methods for analyzing a flow of a fluid at two or more discrete locations to determine a characteristic of a substance in the fluid.

The exemplary systems and methods described herein employ various configurations of optical computing devices, also commonly referred to as "opticoanalytical devices," for the real-time or near real-time monitoring of fluids. The disclosed systems and methods may be suitable for use in the oil and gas industry since the described optical computing devices provide a cost-effective, rugged, and accurate means for monitoring hydrocarbon quality in order to facilitate the efficient management of oil/gas production. It will be appreciated, however, that the various disclosed systems and methods are equally applicable to other technology fields including, but not limited to, the food and drug industry, industrial applications, mining industries, or any field where it may be advantageous to determine in real-time or near real-time the concentration or a characteristic of a specific substance in a flowing fluid.

The optical computing devices disclosed herein, which are described in more detail below, can advantageously provide real-time or near real-time monitoring of fluid flow that cannot presently be achieved with either onsite analyses at a job site or via more detailed analyses that take place in a laboratory. A significant and distinct advantage of these devices is that they can be configured to specifically detect and/or measure a particular component or characteristic of interest of a fluid, thereby allowing qualitative and/or quantitative analyses of the fluid to occur without having to undertake a time-consuming sample processing procedure. With real-time or near real-time analyses on hand, the exemplary systems and methods described herein may be able to provide some measure of proactive or responsive control over the fluid flow, enable the collection and archival of fluid information in conjunction with operational information to optimize subsequent operations, and/or enhance the capacity for remote job execution.

The optical computing devices suitable for use in the present embodiments can be deployed at two or more fluidly communicable points within a flow path to monitor the fluid and the various changes that may occur thereto between the two or more points. In some cases, for example, the optical computing devices can be used to monitor changes to a fluid that take place over time or a predetermined distance in the flow path. In some cases, the optical computing devices can be used to monitor changes to the fluid as a result of adding a treatment substance thereto, removing a treatment substance therefrom, or exposing the fluid to a condition that potentially changes a characteristic of the fluid in some way. In some cases, quality control information regarding treatment substances can be obtained, for example, before and after introduction into the flow path. Thus, the systems and methods described herein may be configured to monitor a flow of fluids and, more particularly, to monitor any changes thereto as a result of adding one or more treatment substances to the fluid at different points in a flow path in order to determine the concentration or effectiveness of the one or more treatment substances. In at least one aspect, this may prove advantageous in verifying a correct dosage of the one or more treatment substances as intended.

In some cases, quality control information regarding the mixing of produced fluids from different wells, different fields, or different operators can be monitored to determine if the mixing is producing a resultant fluid with a higher instance of deposit formation in the flow path through which the mixed fluids are flowing. In some cases, quality control information regarding the quality of produced fluids can be monitored, whereby if one field or operator's production has a higher quality of hydrocarbon than another, accurate financial models can be built with regards to the sharing, leasing, and/or license payment for use of shared transportation and production facilities.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Fluids can include various flowable mixtures of solids, liquids and/or gases. Illustrative gases that can be considered fluids according to the present embodiments include, for example, air, nitrogen, carbon dioxide, argon, helium, methane, ethane, butane, and other hydrocarbon gases, combinations thereof and/or the like.

As used herein, the term "characteristic" refers to a chemical, mechanical, or physical property of a substance. A characteristic of a substance may include a quantitative value of one or more chemical components therein. Such chemical components may be referred to herein as "analytes." Illustrative characteristics of a substance that can be monitored with the optical computing devices disclosed herein can include, for example, chemical composition (e.g., identity and concentration in total or of individual components), impurity content, pH, viscosity, density, ionic strength, total dissolved solids, salt content, porosity, opacity, bacteria content, phase state (i.e., solid, liquid, gas, plasma), combinations thereof, and the like. Moreover, the phrase "characteristic of interest of/in a fluid" may be used herein to refer to the characteristic of a substance contained in or otherwise flowing with the fluid.

As used herein, the term "flow path" refers to a route through which a fluid is capable of being transported between two points. In some cases, the flow path need not be continuous or otherwise contiguous between the two points. Exemplary flow paths include, but are not limited to, a flowline, a pipeline, a hose, a process facility, a storage vessel, a transport vessel, a trough, a stream, a sewer, a subterranean formation, a flow conduit, a wellbore, etc., combinations thereof, or the like. In cases where the flow path is a pipeline, or the like, the pipeline may be a pre-commissioned pipeline or an operational pipeline. It should be noted that the term flow path does not necessarily imply that a fluid is flowing therein, rather that a fluid is capable of being transported or otherwise flowable therethrough.

As used herein, the term "substance," or variations thereof, refers to at least a portion of a matter or material of interest to be evaluated using the optical computing devices described herein. In some embodiments, the substance is the characteristic of interest, as defined above, and may include any integral component of the fluid flowing within the flow path. For example, the substance may include compounds containing elements such as barium, calcium, manganese, sulfur, iron, strontium, chlorine, etc, and any other chemical substance that can lead to precipitation within a flow path. The substance may also refer to paraffins, waxes, asphaltenes, aromatics, saturates, foams, salts, particulates, sand or other solid particles, combinations thereof, and the like. In yet other embodiments, in terms of quantifying ionic strength, the substance may include various ions, such as, but not limited to, $Ba_2^+$, $Sr_2^+$, $Fe^+$, $Fe_2^+$ (or total Fe), $Mn_2^+$, $SO_4^{2-}$, $CO_3^{2-}$, $Ca_2^+$, $Mg_2^+$, $Na^+$, $K^+$, $Cl^-$.

In other aspects, the substance may include any substance added to the flow path in order to treat the flow path for flow assurance reasons. Exemplary treatment substances may include, but are not limited to, acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, fluid loss control additives, gases, catalysts, clay control agents, chelating agents, corrosion inhibitors, dispersants, flocculants, scavengers (e.g., $H_2S$ scavengers, $CO_2$ scavengers or $O_2$ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, and the like. Combinations of these substances can be referred to as a substance as well.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a substance or sample of the substance, and produce an output of electromagnetic radiation from a processing element arranged within the optical computing device. The processing element may be, for example, an integrated computational element (ICE) used in the optical computing device. As discussed in greater detail below, the electromagnetic radiation that optically interacts with the processing element is changed so as to be readable by a detector, such that an output of the detector can be correlated to at least one characteristic of the substance being measured or monitored. The output of electromagnetic radiation from the processing element can be reflected electromagnetic radiation, transmitted electromagnetic radiation, and/or dispersed electromagnetic radiation. Whether reflected or transmitted electromagnetic radiation is analyzed by the detector may be dictated by the structural parameters of the optical computing device as well as other considerations known to those skilled in the art. In addition, emission and/or scattering of the substance, for example via fluorescence, luminescence, Raman scattering, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to electromagnetic radiation that has been reflected, transmitted, scattered, diffracted, or absorbed by, emitted, or re-radiated, for example, using the integrated computational elements, but may also apply to interaction with a fluid or a substance in the fluid.

The exemplary systems and methods described herein will include at least two optical computing devices strategically arranged along a flow path in order to monitor a fluid flowing therein and calculate concentration differences between measurement or monitoring locations. Each optical computing device may include an electromagnetic radiation source, at least one processing element (e.g., integrated computational elements), and at least one detector arranged to receive optically interacted light from the at least one processing element. As disclosed below, however, in at least one embodiment, the electromagnetic radiation source may be omitted and instead the electromagnetic radiation may be derived from the fluid or substance itself. In some embodiments, the exemplary optical computing devices may be specifically configured for detecting, analyzing, and quantitatively measuring a particular characteristic or analyte of interest of the fluid in the flow path. In other embodiments, the optical computing devices may be general purpose optical devices, with post-acquisition processing (e.g., through computer means) being used to specifically detect the characteristic of the sample.

In some embodiments, suitable structural components for the exemplary optical computing devices are described in commonly owned U.S. Pat. Nos. 6,198,531; 6,529,276; 7,123,844; 7,834,999; 7,911,605, 7,920,258, and 8,049,881, each of which is incorporated herein by reference in its entirety, and U.S. patent application Ser. Nos. 12/094,460; 12/094,465; and 13/456,467, each of which is also incorporated herein by reference in its entirety. As will be appreciated, variations of the structural components of the optical computing devices described in the above-referenced patents and patent applications may be suitable, without departing from the scope of the disclosure, and therefore, should not be considered limiting to the various embodiments disclosed herein.

The optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically configured to detect and analyze particular characteristics and/or analytes of interest of a fluid or a substance in the fluid. As a result, interfering signals are discriminated from those of interest in the substance by appropriate configuration of the optical computing devices, such that the optical computing devices provide a rapid response regarding the characteristics of the fluid or substance as based on the detected output. In some embodiments, the detected output can be converted into a voltage that is distinctive of the magnitude of the characteristic being monitored in the fluid. The foregoing advantages and others make the optical computing devices particularly well suited for field and downhole use.

The optical computing devices can be configured to detect not only the composition and concentrations of a substance in a fluid, but they also can be configured to determine physical properties and other characteristics of the substance as well, based on their analysis of the electromagnetic radiation received from the substance. For example, the optical computing devices can be configured to determine the concentration of an analyte and correlate the determined concentration to a characteristic of a substance by using suitable processing means. As will be appreciated, the optical computing devices may be configured to detect as many characteristics or analytes as desired for a given substance or fluid. All that is required to accomplish the monitoring of multiple characteristics or analytes is the incorporation of suitable processing and detection means within the optical computing device for each characteristic or analyte. In some embodiments, the properties of the substance can be a combination of the properties of the analytes therein (e.g., a linear, non-linear, logarithmic, and/or exponential combination). Accordingly, the more characteristics and analytes that are detected and analyzed using the optical computing devices, the more accurately the properties of the given substance will be determined.

The optical computing devices described herein utilize electromagnetic radiation to perform calculations, as opposed to the hardwired circuits of conventional electronic processors. When electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. The optical computing devices described herein are capable of extracting the information of the spectral fingerprint of multiple characteristics or analytes within a substance and converting that information into a detectable output regarding the overall properties of the substance. That is, through suitable configurations of the optical computing devices, electromagnetic radiation associated with characteristics or analytes of interest in a substance can be separated from electromagnetic radiation associated with all other components of the substance in order to estimate the properties of the substance in real-time or near real-time.

Figure 1:
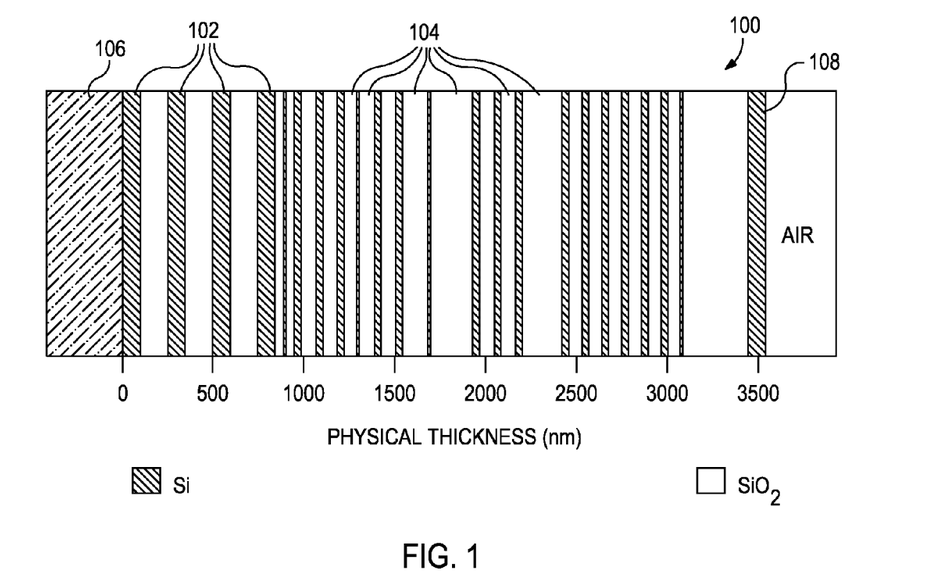
FIG. 1 illustrates an exemplary integrated computation element, according to one or more embodiments.

The processing elements used in the exemplary optical computing devices described herein may be characterized as integrated computational elements (ICE). Each ICE is capable of distinguishing electromagnetic radiation related to the characteristic or analyte of interest from electromagnetic radiation related to other components of a substance. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the substance using a conventional spectroscopic instrument. The spectrum of interest of a given characteristic of a substance typically includes any number of different wavelengths. It should be understood that the exemplary ICE 100 in FIG. 1 does not in fact represent any particular characteristic of a given substance, but is provided for purposes of illustration only. Consequently, the number of layers 102, 104 and their relative thicknesses, as shown in FIG. 1, bear no correlation to any particular characteristic of a given substance. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the substance.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary integrated computational elements (also referred to as multivariate optical elements) is provided in *Applied Optics*, Vol. 35, pp. 5484-5492 (1996) and Vol. 129, pp. 2876-2893, which is hereby incorporated by reference.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest. Further details regarding how the exemplary ICE 100 is able to distinguish and process electromagnetic radiation related to the characteristic or analyte of interest are described in U.S. Pat. Nos. 6,198,531; 6,529,276; and 7,920,258, previously incorporated herein by reference.

Figure 2:
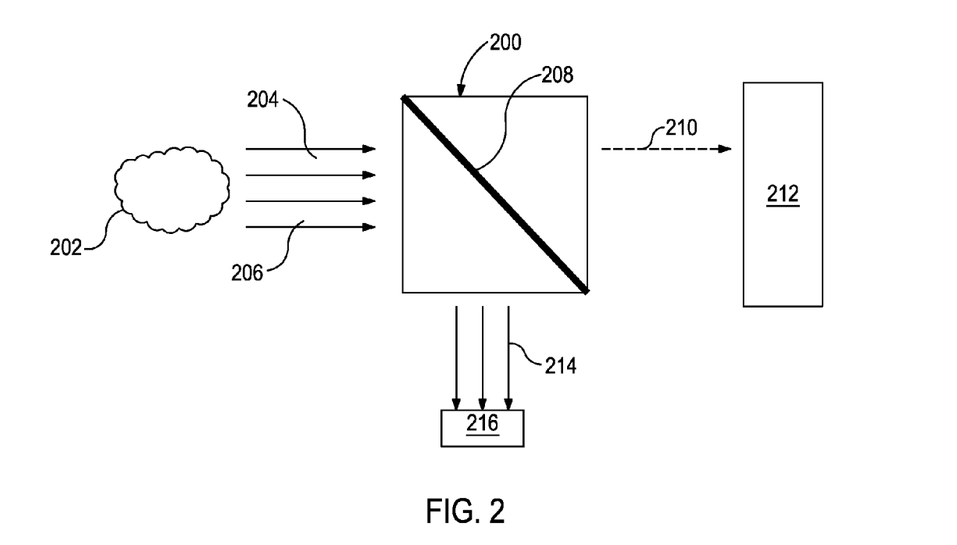
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic of a substance from other electromagnetic radiation. As shown in FIG. 2, after being illuminated with incident electromagnetic radiation, a substance 202 containing an analyte of interest (e.g., a characteristic of the substance) produces an output of electromagnetic radiation (e.g., sample-interacted light), some of which is electromagnetic radiation 204 corresponding to the characteristic or analyte of interest and some of which is background electromagnetic radiation 206 corresponding to other components or characteristics of the substance 202.

Although not specifically shown, one or more spectral elements may be employed in the device 200 in order to restrict the optical wavelengths and/or bandwidths of the system and thereby eliminate unwanted electromagnetic radiation existing in wavelength regions that have no importance. Such spectral elements can be located anywhere along the optical train, but are typically employed directly after the light source, which provides the initial electromagnetic radiation. Various configurations and applications of spectral elements in optical computing devices may be found in commonly owned U.S. Pat. Nos. 6,198,531; 6,529,276; 7,123,844; 7,834,999; 7,911,605; 7,920,258, 8,049,881, and U.S. patent application Ser. No. 12/094,460 (U.S. Pat. App. Pub. No. 2009/0219538); Ser. No. 12/094,465 (U.S. Pat. App. Pub. No. 2009/0219539); and Ser. No. 13/456,467, incorporated herein by reference, as indicated above.

The beams of electromagnetic radiation 204, 206 impinge upon the optical computing device 200, which contains an exemplary ICE 208 therein. In the illustrated embodiment, the ICE 208 may be configured to produce optically interacted light, for example, transmitted optically interacted light 210 and reflected optically interacted light 214. In operation, the ICE 208 may be configured to distinguish the electromagnetic radiation 204 from the background electromagnetic radiation 206.

The transmitted optically interacted light 210, which may be related to the characteristic or analyte of interest of the substance 202, may be conveyed to a detector 212 for analysis and quantification. In some embodiments, the detector 212 is configured to produce an output signal in the form of a voltage that corresponds to the particular characteristic of the substance 202. In at least one embodiment, the signal produced by the detector 212 and the concentration of the characteristic of the substance 202 may be directly proportional. In other embodiments, the relationship may be a polynomial function, an exponential function, and/or a logarithmic function. The reflected optically interacted light 214, which may be related to the characteristic and other components of the substance 202, can be directed away from detector 212. In alternative configurations, the ICE 208 may be configured such that the reflected optically interacted light 214 can be related to the analyte of interest, and the transmitted optically interacted light 210 can be related to other components of the substance 202.

In some embodiments, a second detector 216 can be present and arranged to detect the reflected optically interacted light 214. In other embodiments, the second detector 216 may be arranged to detect the electromagnetic radiation 204, 206 derived from the substance 202 or electromagnetic radiation directed toward or before the substance 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204, 206, and the transmitted or reflected electromagnetic radiation can then be directed to one or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before travelling to the detector 212.

The characteristic(s) of the substance 202 being analyzed using the optical computing device 200 can be further processed computationally to provide additional characterization information about the substance 202. In some embodiments, the identification and concentration of each analyte in the substance 202 can be used to predict certain physical characteristics of the substance 202. For example, the bulk characteristics of a substance 202 can be estimated by using a combination of the properties conferred to the substance 202 by each analyte.

In some embodiments, the concentration of each analyte or the magnitude of each characteristic determined using the optical computing device 200 can be fed into an algorithm operating under computer control. The algorithm may be configured to make predictions on how the characteristics of the substance 202 change if the concentrations of the analytes are changed relative to one another. In some embodiments, the algorithm can produce an output that is readable by an operator who can manually take appropriate action, if needed, based upon the output. In some embodiments, the algorithm can take proactive process control by automatically adjusting the flow of a treatment substance being introduced into a flow path or by halting the introduction of the treatment substance in response to an out of range condition.

The algorithm can be part of an artificial neural network configured to use the concentration of each detected analyte in order to evaluate the characteristic(s) of the substance 202 and predict how to modify the substance 202 in order to alter its properties in a desired way. Illustrative but non-limiting artificial neural networks are described in commonly owned U.S. patent application Ser. No. 11/986,763 (U.S. Patent Application Publication 2009/0182693), which is incorporated herein by reference. It is to be recognized that an artificial neural network can be trained using samples of substances having known concentrations, compositions, and/or properties, and thereby generating a virtual library. As the virtual library available to the artificial neural network becomes larger, the neural network can become more capable of accurately predicting the characteristics of a substance having any number of analytes present therein. Furthermore, with sufficient training, the artificial neural network can more accurately predict the characteristics of the substance, even in the presence of unknown analytes.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

Figure 3:
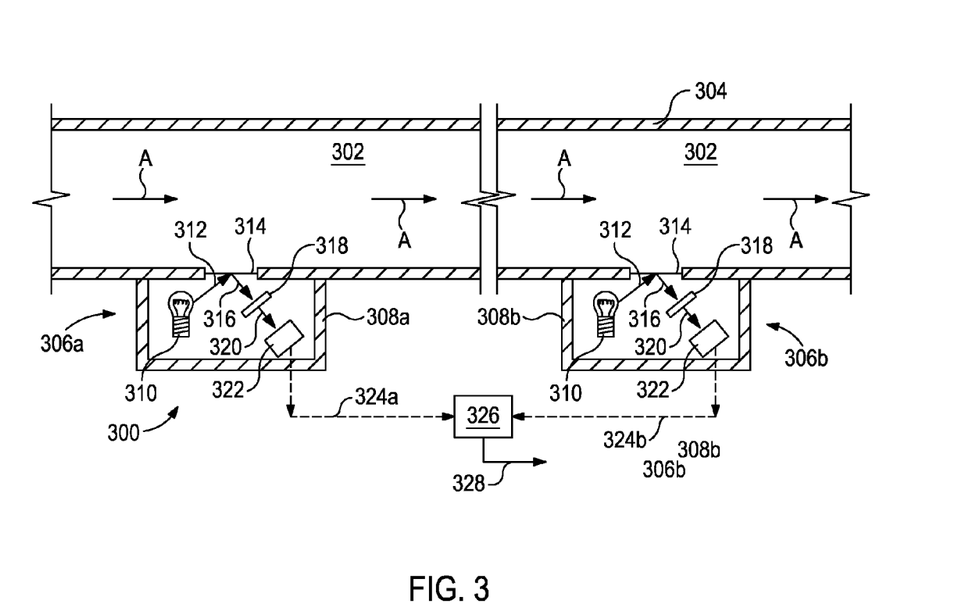
FIG. 3 illustrates an exemplary system for monitoring a fluid present in a flow path, according to one or more embodiments.

Referring now to FIG. 3, illustrated is an exemplary system 300 for monitoring a fluid 302, according to one or more embodiments. In the illustrated embodiment, the fluid 302 may be contained or otherwise flowing within an exemplary flow path 304. The flow path 304 may be a flow line or a pipeline and the fluid 302 present therein may be flowing in the general direction indicated by the arrows A (i.e., from upstream to downstream). As will be appreciated, however, the flow path 304 may be any other type of flow path, as generally described or otherwise defined herein. In at least one embodiment, however, the flow path 304 may form part of an oil/gas pipeline and may be part of a wellhead or a plurality of subsea and/or above-ground interconnecting flow lines or pipes that interconnect various subterranean hydrocarbon reservoirs with one or more receiving/gathering platforms or process facilities. In some embodiments, portions of the flow path 304 may be employed downhole and fluidly connect, for example, a formation and a wellhead. As such, portions of the flow path 304 may be arranged substantially vertical, substantially horizontal, or any directional configuration therebetween, without departing from the scope of the disclosure.

The system 300 may include at least a first optical computing device 306a and a second optical computing device 306b.

The optical computing devices 306a,b may be similar in some respects to the optical computing device 200 of FIG. 2, and therefore may be best understood with reference thereto. As illustrated, the first and second optical computing devices 306a,b may each be associated with the flow path 304 at independent and distinct monitoring locations along the length of the flow path 304. Specifically, the first optical computing device 306a may be located at a first monitoring location along the flow path 304 and the second optical computing device 306b may be located at a second monitoring location along the flow path 304, where the first monitoring location fluidly communicates with the second monitoring location via contiguous portions of the flow path 304. As described in greater detail below, each optical computing device 306a,b may be useful in determining a particular characteristic of the fluid 302 within the flow path 304, such as determining a concentration of a substance that may be present within the fluid 302 at the corresponding location along the flow path 304.

In some embodiments, the second optical computing device 306b is arranged at a predetermined distance from the first optical computing device 306a along the length of the flow path 304. In other embodiments, however, the first optical computing device 306a may be randomly spaced from the second optical computing device 306b, without departing from the scope of the disclosure. Moreover, while only two optical computing devices 306a,b are shown in FIG. 3, it will be appreciated that the system 300 may employ more than two optical computing devices within the flow path 304. In such embodiments, each additional optical computing device may be spaced from the first and second optical computing devices 306a,b at predetermined or random distances, depending on the application.

Each device 306a,b may be housed within an individual casing or housing coupled or otherwise attached to the flow path 304 at its respective location. As illustrated, for example, the first device 306a may be housed within a first housing 308a and the second device 306b may be housed within a second housing 308b. In some embodiments, the first and second housings 308a,b may be mechanically coupled to the flow path 304 using, for example, mechanical fasteners, brazing or welding techniques, adhesives, magnets, combinations thereof or the like. Each housing 308a,b may be configured to substantially protect the internal components of the respective devices 306a,b from damage or contamination from the external environment. Moreover, each housing 308a,b may be designed so as to withstand the pressures that may be experienced within the flow path 304 and thereby provide a fluid tight seal between the flow path 304 and the respective housing 308a,b.

Each device 306a,b may include an electromagnetic radiation source 310 configured to emit or otherwise generate electromagnetic radiation 312. The electromagnetic radiation source 310 may be any device capable of emitting or generating electromagnetic radiation, as defined herein. For example, the electromagnetic radiation source 310 may be a light bulb, a light emitting device (LED), a laser, a blackbody, a photonic crystal, an X-Ray source, combinations thereof, or the like. In some embodiments, a lens (not shown), or any other type of optical device configured to transmit or otherwise convey electromagnetic radiation, may be arranged to collect or otherwise receive the electromagnetic radiation 312 and direct a beam of the same toward the fluid 302.

In one or more embodiments, the devices 306a,b may also include a sampling window 314 arranged adjacent the fluid 302 for detection purposes. The sampling window 314 may be made from a variety of transparent, rigid or semi-rigid materials that are configured to allow transmission of the electromagnetic radiation 312 therethrough. For example, the sampling window 314 may be made of, but is not limited to, glasses, plastics, semi-conductors, crystalline materials, polycrystalline materials, hot or cold-pressed powders, combinations thereof, or the like. In order to remove ghosting or other imaging issues resulting from reflectance on the sampling window 314, the system 300 may employ one or more internal reflectance elements (IRE), such as those described in co-owned U.S. Pat. No. 7,697,141, and/or one or more imaging systems, such as those described in co-owned U.S. patent application Ser. No. 13/456,467, the contents of each hereby being incorporated by reference.

After passing through the sampling window 314, the electromagnetic radiation 312 impinges upon and optically interacts with the fluid 302, or a substance flowing within the fluid 302. As a result, optically interacted radiation 316 is generated by and reflected from the fluid 302. Those skilled in the art, however, will readily recognize that alternative variations of the devices 306a,b may allow the optically interacted radiation 316 to be generated by being transmitted, scattered, diffracted, absorbed, emitted, or re-radiated by and/or from the fluid 302, or the particular substance flowing within the fluid 302, without departing from the scope of the disclosure.

The optically interacted radiation 316 in each device 306a,b may be directed to or otherwise be received by an ICE 318 arranged within the corresponding device 306a,b. Each ICE 318 may be a spectral component substantially similar to the ICE 100 described above with reference to FIG. 1. Accordingly, in operation each ICE 318 may be configured to receive the optically interacted radiation 316 and produce modified electromagnetic radiation 320 corresponding to a particular characteristic or analyte of interest of the fluid 302. In particular, the modified electromagnetic radiation 320 is electromagnetic radiation that has optically interacted with the ICE 318, whereby an approximate mimicking of the regression vector corresponding to the characteristic of interest of the fluid 302 is obtained.

It should be noted that, while FIG. 3 depicts the ICE 318 as receiving reflected electromagnetic radiation from the sampling window 314 and the fluid 302, the ICE 318 may be arranged at any point along the optical train of the device 306a,b, without departing from the scope of the disclosure. For example, in one or more embodiments, the ICE 318 may be arranged within the optical train prior to the sampling window 314 and equally obtain substantially the same results. In other embodiments, the sampling window 314 may serve a dual purpose as both a transmission window and the ICE 318 (i.e., a spectral component). In yet other embodiments, the ICE 318 may generate the modified electromagnetic radiation 320 through reflection, instead of transmission therethrough.

Moreover, while only one ICE 318 is shown in each corresponding device 306a,b, embodiments are contemplated herein which include the use of at least two ICE in each device 306a,b configured to cooperatively determine the characteristic of interest in the fluid 302. For example, two or more ICE may be arranged in series or parallel within the device 306a,b and configured to receive the optically interacted radiation 316 and thereby enhance sensitivities and detector limits of the device 306a,b. In other embodiments, two or more ICE may be arranged on a movable assembly, such as a rotating disc or an oscillating linear array, which moves such that individual ICE components are able to be exposed to or otherwise optically interact with electromagnetic radiation for a distinct brief period of time. In one or more embodiments, the two or more ICE in any of these embodiments may be configured to be either associated or disassociated with the characteristic of interest in the fluid 302. In other embodiments, the two or more ICE may be configured to be positively or negatively correlated with the characteristic of interest in the fluid 302. These optional embodiments employing two or more ICE 318 are further described in co-pending U.S. patent application Ser. Nos. 13/456,264 and 13/456,405, the contents of which are hereby incorporated by reference in their entireties.

In some embodiments, it may be desirable to monitor more than one analyte or characteristic of interest at a time at each location along the flow path 304. In such embodiments, various configurations for multiple ICE components can be used, where each ICE component is configured to detect a particular and/or distinct characteristic or analyte of interest. In some embodiments, the characteristic or analyte can be analyzed sequentially using multiple ICE components that are provided a single beam of electromagnetic radiation being reflected from or transmitted through the fluid 302. In some embodiments, as briefly mentioned above, multiple ICE components can be arranged on a rotating disc, where the individual ICE components are only exposed to the beam of electromagnetic radiation for a short time. Advantages of this approach can include the ability to analyze multiple analytes using a single optical computing device and the opportunity to assay additional analytes simply by adding additional ICE components to the rotating disc. In various embodiments, the rotating disc can be turned at a frequency of about 10 RPM to about 30,000 RPM such that each analyte in the fluid 302 is measured rapidly. In some embodiments, these values can be averaged over an appropriate time domain (e.g., about 1 millisecond to about 1 hour) to more accurately determine the characteristics of the fluid 302.

In other embodiments, multiple optical computing devices can be placed in parallel at each location along the length of the flow path 304, where each optical computing device contains a unique ICE that is configured to detect a particular characteristic or analyte of interest of the fluid 302. In such embodiments, a beam splitter can divert a portion of the electromagnetic radiation being reflected by, emitted from, or transmitted through the fluid 302 and into each optical computing device. Each optical computing device, in turn, can be coupled to a corresponding detector or detector array that is configured to detect and analyze an output of electromagnetic radiation from the optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two optical computing devices having a rotating disc with a plurality of ICE components arranged thereon can be placed in series for performing an analysis at a single location along the length of the flow path 304. Likewise, multiple detection stations, each containing optical computing devices in parallel, can be placed in series for performing a similar analysis.

The modified electromagnetic radiation 320 generated by each ICE 318 may subsequently be conveyed to a detector 322 for quantification of the signal. The detector 322 may be any device capable of detecting electromagnetic radiation, and may be generally characterized as an optical transducer. In some embodiments, the detector 322 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 322 in each device 306a,b may be configured to produce an output signal in real-time or near real-time in the form of a voltage (or current) that corresponds to the particular characteristic of interest in the fluid 302. For example, the detector 322 arranged within the first device 306a may generate a first output signal 324a, and the detector 322 arranged within the second device 306b may generate a second output signal 324b. The voltage returned by each detector 322 is essentially the dot product of the optical interaction of the optically interacted radiation 316 with the respective ICE 318 as a function of the concentration of the characteristic of interest of the fluid 302. As such, each output signal 324a,b produced by its corresponding detector 322 and the concentration of the characteristic of interest in the fluid 302 may be related.

The output signal 324a,b from each device 306a,b may be conveyed to or otherwise received by a signal processor 326 communicably coupled to the detectors 322. The signal processor 326 may be a computer including a non-transitory machine-readable medium, and may employ an algorithm configured to calculate or otherwise determine the differences between the two output signals 324a,b. For example, the first output signal 324a may be indicative of the concentration of a substance and/or the magnitude of the characteristic of interest in the fluid 302 at the location of the first device 306a along the flow path 304, and the second output signal 324b may be indicative of the concentration of the substance and/or the magnitude of the characteristic of interest in the fluid 302 at the location of the second device 306b along the flow path 304. Accordingly, the signal processor 326 may be configured to determine how the concentration of the substance and/or the magnitude of the characteristic of interest in the fluid 302 has changed between the first and second monitoring locations along the flow path 304. In some embodiments, the algorithm employed by the signal processor 326 may take into account the distance between the two devices 306a,b. Depending upon the application, the monitoring distances may be short (e.g., meters or even centimeters), or long (e.g., thousands of miles), mainly depending on the application of interest. For those knowledgeable in the art, they will also appreciate that multiple monitors may be employed at a variety of points along the flow path 304.

In real-time or near real-time, the signal processor 326 may be configured to provide a resulting output signal 328 corresponding to the measured difference in the substance and/or the magnitude of the characteristic of interest in the fluid 302 between the first and second monitoring locations along the flow path 304. In some embodiments, the resulting output signal 328 may be conveyed, either wired or wirelessly, to a user for consideration. In other embodiments, the resulting output signal 328 may be recognized by the signal processor 326 as being within or without a predetermined or preprogrammed range of suitable operation. If the resulting output signal 328 exceeds the predetermined or preprogrammed range of operation, the signal processor 326 may be configured to alert the user so appropriate corrective action may be taken, or otherwise autonomously undertake the appropriate corrective action such that the resulting output signal 328 returns to a value within the predetermined or preprogrammed range of operation.

Those skilled in the art will readily appreciate the various and numerous applications that the system 300, and alternative configurations thereof, may be suitably used with. For example, in one or more embodiments, the first and second output signals 324a,b may be indicative of a concentration of a substance flowing with the fluid 302 at the first and second monitoring locations, respectively. In some embodiments, the substance, which may be a corrosion or scale inhibitor, may be added to the fluid 302 at or near the first monitoring location where the first optical computing device 306a is arranged. The first optical computing device 306a may be configured to determine and report the concentration of the substance at the first monitoring location. Likewise, the second optical computing device 306b may be configured to determine and report the concentration of the substance at the second monitoring location, downstream from the first monitoring location. By calculating the difference between the first and second output signals 324a,b, the signal processor 326 may be able to determine whether the added substance is operating as intended within the flow path 304 or otherwise whether the added dosage was sufficient.

In other embodiments, the first and second output signals 324a,b may be indicative of a characteristic of interest of the fluid 302 itself at the first and second monitoring locations, respectively. For example, the fluid 302 may include one or more chemicals or chemical compositions, such as paraffin or calcium carbonate, that precipitate under certain conditions and form scale on the inner walls of the flow path 304. The first optical computing device 306a may be configured to determine and report the concentration of the one or more chemicals or chemical compositions at the first monitoring location. Likewise, the second optical computing device 306b may be configured to determine and report the concentration of the one or more chemicals or chemical compositions at the second monitoring location, downstream from the first monitoring location. By calculating the difference between the first and second output signals 324a,b, the signal processor 326 may be able to determine how much scale is being deposited on the walls of the flow path and, more importantly, generally where this is occurring.

In other embodiments, the first and second output signals 324a,b may be indicative of other characteristics, such as, but not limited to, pH, viscosity, density or specific gravity, and ionic strength, as measured at the first and second monitoring locations, respectively.

In yet further embodiments, the system 300 may be used to monitor production from two or more hydrocarbon-producing fields. For example, it is often common that corresponding flow paths extending from two or more hydrocarbon-producing fields eventually join downstream and ultimately share a common pipeline that conveys the combined produced fluids to a gathering or production facility. As a result, the fluids produced from each hydrocarbon-producing field are mixed within the common pipeline, and such mixing of the produced fluids may cause deposits to form in the common pipeline due to incompatibility of the different produced fluids. In some applications, the first and second optical computing devices 306a,b may be arranged on corresponding first and second flow paths 304 (i.e., pipelines or flow lines), where the first and second flow paths 304 eventually join downstream into a common pipeline (not shown). The first and second output signals 324a,b may be indicative of a characteristic of interest of the fluid 302 in each of the first and second flow paths 304. By analyzing the first and second output signals 324a,b, an operator of the common pipeline may be able to determine the origin of deposits or other harmful substances found within the common pipeline. If the origin of the deposits or other harmful substances is shown to correspond to the first flow path 304, for instance, the cost of chemical inhibition or cleaning can be charged to the owner of the first flow path 304.

Figure 4:
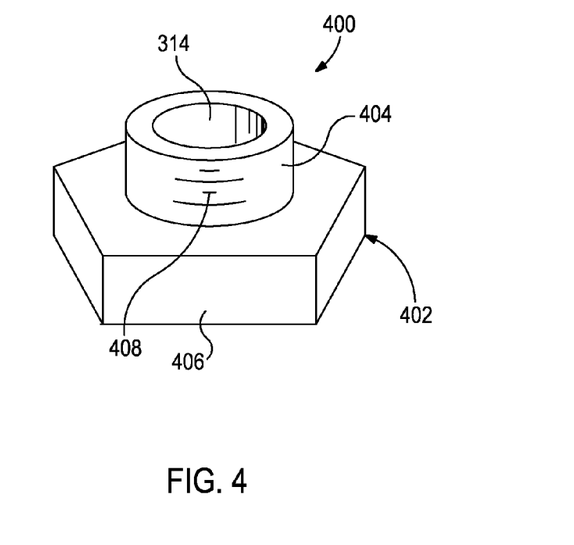
FIG. 4 illustrates an exemplary housing that may be used to house an optical computing device, according to one or more embodiments.

Referring now to FIG. 4, illustrated is an exemplary housing 400 that may be used to house an optical computing device, according to one or more embodiments. The housing 400 may serve the same purpose as the first and second housings 308a and 308b discussed above with reference to FIG. 3 and, in at least one embodiment, may be an alternative embodiment for each housing 308a,b. Those skilled in the art, however, will readily recognize that several alternative designs and configurations of housings used to house the optical computing devices are suitable for the presently disclosed systems and methods. Indeed, the housing embodiments described and disclosed herein are by way of example only, and should not be considered limiting to the exemplary systems and methods disclosed herein.

As illustrated, the housing 400 may be in the form of a bolt 402 which encloses the various components of an optical computing device, such as the first and second optical computing devices 306a,b of FIG. 3. In one embodiment, the components of the optical computing device housed within the housing 400 may be housed within a stem 404 of the bolt 402, and the bolt 402 may have a hex head 406 for manual manipulation of the housing 400 using, for example, a wrench or other suitable torque-generating hand tool.

In at least one embodiment, the housing 400 has external threads 408 that are threadable with corresponding mating pipe threads (not shown) provided in, for example, an opening defined in the flow path 304 (FIG. 3) that is configured to receive the housing 400. The threads 408 may be sealed to the mating pipe threads with a thread sealant in order to help withstand the elevated pressures that may be experienced in the flow path 304. The sampling window 314 is configured to be in optical communication with the fluid 302 (FIG. 3) and allows optical interaction between the fluid 302 and the other internal components of the internally-housed optical computing device.

Referring again to FIG. 3, those skilled in the art will readily recognize that, in one or more embodiments, electromagnetic radiation may be derived from the fluid 302 itself, and otherwise derived independent of the electromagnetic radiation source 310. For example, various substances naturally radiate electromagnetic radiation that is able to optically interact with the ICE 318. In some embodiments, for example, the fluid 302 or the substance within the fluid 302 may be a blackbody radiating substance configured to radiate heat that may optically interact with the ICE 318. In other embodiments, the fluid 302 or the substance within the fluid 302 may be radioactive or chemo-luminescent and, therefore, radiate electromagnetic radiation that is able to optically interact with the ICE 318. In yet other embodiments, the electromagnetic radiation may be induced from the fluid 302 or the substance within the fluid 302 by being acted upon mechanically, magnetically, electrically, combinations thereof, or the like. For instance, in at least one embodiment, a voltage may be placed across the fluid 302 or the substance within the fluid 302 in order to induce the electromagnetic radiation. As a result, embodiments are contemplated herein where the electromagnetic radiation source 310 is omitted from the particular optical computing device.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A system, comprising:
a flow path containing a fluid and providing at least a first monitoring location and a second monitoring location;
a first optical computing device arranged at the first monitoring location and having a first integrated computational element configured to optically interact with the fluid and convey optically interacted light to a first detector which generates a first output signal corresponding to a characteristic of the fluid at the first monitoring location;
a second optical computing device arranged at the second monitoring location and having a second integrated computational element configured to optically interact with the fluid and convey optically interacted light to a second detector which generates a second output signal corresponding to the characteristic of the fluid at the second location; and
a signal processor communicably coupled to the first and second detectors and configured to receive the first and second output signals and determine a difference between the first and second output signals, wherein at least one of the first or second integrated computational elements comprises a plurality of alternating layers of two different materials, the two different materials are selected from the group consisting of silicon, silica ($SiO_2$), quartz, niobia, niobium, germanium, germania, and magnesium fluoride, a thickness of each of the plurality of alternating layers is selected according to a spectral attribute of the characteristic of the fluid, and a portion of the optically interacted light is transmitted through the at least one of the first or second integrated computational elements.

2. The system of claim 1, wherein the first monitoring location fluidly communicates with the second monitoring location via contiguous portions of the flow path.

3. The system of claim 1, wherein the first and second optical computing devices are housed within corresponding first and second housings, the first and second housings being coupled to the flow path at the first and second monitoring locations, respectively.

4. The system of claim 1, wherein the first and second optical computing devices further include corresponding first and second electromagnetic radiation sources configured to emit electromagnetic radiation to optically interact with the fluid.

5. The system of claim 1, wherein the difference between the first and second output signals is indicative of how the characteristic of the fluid changed between the first and second monitoring locations.

6. The system of claim 5, wherein the characteristic of the fluid is one or more chemicals or chemical compositions present in the fluid.

7. The system of claim 6, wherein the one or more chemicals or chemical compositions include at least one of paraffins, waxes, asphaltenes, aromatics, saturates foams, salts, particulates, and sand.

8. The system of claim 6, wherein the one or more chemicals or chemical compositions include at least one of barium, calcium, manganese, sulfur, iron, strontium, and chlorine.

9. The system of claim 5, wherein the characteristic of the fluid corresponds to a treatment substance added to the fluid and contained within the flow path.

10. The system of claim 9, wherein the treatment substance is selected from the group consisting of acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants, gravel, particulate diverters, salts, fluid loss control additives, gases, catalysts, clay control agents, chelating agents, corrosion inhibitors, dispersants, flocculants, scavengers, lubricants, breakers, delayed release breakers, friction reducers, bridging agents, viscosifiers, weighting agents, solubilizers, rheology control agents, viscosity modifiers, pH control agents, hydrate inhibitors, relative permeability modifiers, diverting agents, consolidating agents, fibrous materials, bactericides, tracers, probes, nanoparticles, derivatives thereof, and the like.

11. The system of claim 9, wherein the difference between the first and second output signals is indicative of how a concentration of the treatment substance changed between the first and second monitoring locations.

12. The system of claim 1, wherein the first output signal and the second output signal are proportional to a vector product of a spectrum of an input light with a regression vector related to the characteristic of the fluid.

13. A method of determining a characteristic of a fluid, comprising:
containing a fluid within a flow path that provides at least a first monitoring location and a second monitoring location;
generating a first output signal corresponding to the characteristic of the fluid at the first monitoring location with a first optical computing device, the first optical computing device having a first integrated computational element configured to optically interact with the fluid and thereby convey optically interacted light to a first detector which generates the first output signal;
generating a second output signal corresponding to the characteristic of the fluid at the second monitoring location with a second optical computing device, the second optical computing device having a second integrated computational element configured to optically interact with the fluid and thereby convey optically interacted light to a second detector which generates the second output signal;
receiving the first and second output signals with a signal processor communicably coupled to the first and second detectors; and
determining a difference between the first and second output signals with the signal processor, wherein at least one of the first or second integrated computational elements comprises a plurality of alternating layers of two different materials, the two different materials are selected from the group consisting of silicon, silica ($SiO_2$), quartz, niobia, niobium, germanium, germania, and magnesium fluoride, a thickness of each of the plurality of alternating layers is selected according to a spectral attribute of the characteristic of the fluid, and a portion of the optically interacted light is transmitted through the at least one of the first or second integrated computational elements.

14. The method of claim 13, wherein determining the difference between the first and second output signals further comprises determining how the characteristic of the fluid changed between the first and second monitoring locations.

15. The method of claim 13, further comprising adding a treatment substance to the flow path, wherein the characteristic of the fluid corresponds to a concentration of the treatment substance.

16. The method of claim 13, wherein determining the difference between the first and second output signals further comprises determining how the concentration of the treatment substance changed between the first and second monitoring locations.

17. The method of claim 13, further comprising:
generating a resulting output signal indicative of a difference between the first and second output signals with the signal processor; and
conveying the resulting output signal to a user for consideration.

18. The method of claim 13, wherein generating the first output signal further comprises:
emitting electromagnetic radiation from a first electromagnetic radiation source;
optically interacting the electromagnetic radiation from the first electromagnetic radiation source with the fluid; and
generating optically interacted electromagnetic radiation to be detected by the first detector.

19. The method of claim 18, wherein generating the second output signal further comprises:
emitting electromagnetic radiation from a second electromagnetic radiation source;
optically interacting the electromagnetic radiation from the second electromagnetic radiation source with the fluid; and
generating optically interacted electromagnetic radiation to be detected by the second detector.

20. A system, comprising:
a first flow path containing a first fluid and providing a first monitoring location;
a second flow path containing a second fluid and providing a second monitoring location, the first and second flow paths being combined downstream into a common flow path conveying the first and second fluids as a combined fluid;
a first optical computing device arranged at the first monitoring location and having a first integrated computational element configured to optically interact with the first fluid and generate a first output signal corresponding to a characteristic of the first fluid, from a first optically interacted light;
a second optical computing device arranged at the second monitoring location and having a second integrated computational element configured to optically interact with the fluid and generate a second output signal corresponding to the characteristic of the second fluid, from a second optically interacted light; and
a signal processor communicably coupled to the first and optical computing devices and configured to receive and determine a difference between the first and second output signals, wherein at least one of the first or second integrated computational elements comprises a plurality of alternating layers of two different materials, the two different materials are selected from the group consisting of silicon, silica ($SiO_2$), quartz, niobia, niobium, germanium, germania, and magnesium fluoride, a thickness of each of the plurality of alternating layers is selected according to a spectral attribute of the characteristic of the first or second fluid, and a portion of the first or second optically interacted light is transmitted through the at least one of the first or second integrated computational elements, respectively.

21. The system of claim 20, further comprising a third optical computing device arranged at a third monitoring location in the common flow path, the third optical computing device having a third integrated computational element configured to optically interact with the combined fluid and generate a third output signal corresponding to a characteristic of the combined fluid to be received by the signal processor.

22. A method of determining a characteristic of a fluid, comprising:
containing a first fluid within a first flow path that provides a first monitoring location;
containing a second fluid within a second flow path that provides a second monitoring location, the first and second flow paths being combined downstream into a common flow path conveying the first and second fluids as a combined fluid;
optically interacting a first integrated computational element with the first fluid to generate a first output signal corresponding to a characteristic of the first fluid from a first optically interacted light;
optically interacting a second integrated computational element with the second fluid to generate a second output signal corresponding to a characteristic of the second fluid from a second optically interacted light;
receiving the first and second output signals with a signal processor; and
determining a difference between the first and second output signals with the signal processor, wherein at least one of the first or second integrated computational elements comprises a plurality of alternating layers of two different materials, the two different materials are selected from the group consisting of silicon (Si), silica ($SiO_2$), quartz, niobia, niobium, germanium, germania, and magnesium fluoride, a thickness of each of the plurality of alternating layers is selected according to a spectral attribute of the characteristic of the first or second fluids, and a portion of the first or second optically interacted light is transmitted through the at least one of the first or second integrated computational elements, respectively.

* * * * *